US011980724B2

(12) United States Patent
Meyer et al.

(10) Patent No.: US 11,980,724 B2
(45) Date of Patent: May 14, 2024

(54) ELECTRICAL ARRANGEMENTS FOR SENSOR ASSEMBLIES IN ELECTROMAGNETIC NAVIGATION SYSTEMS

(71) Applicant: Boston Scientific Scimed Inc., Maple Grove, MN (US)

(72) Inventors: Steven J. Meyer, Lake Elmo, MN (US); James E. Blood, Shoreview, MN (US); David A. Chizek, Brooklyn Park, MN (US); Matthew Hein, Eden Prairie, MN (US); Daniel J. Foster, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 61 days.

(21) Appl. No.: 17/480,086

(22) Filed: Sep. 20, 2021

(65) Prior Publication Data
US 2022/0001140 A1    Jan. 6, 2022

Related U.S. Application Data

(63) Continuation of application No. 16/248,352, filed on Jan. 15, 2019, now Pat. No. 11,141,567.
(Continued)

(51) Int. Cl.
*A61M 25/01* (2006.01)
*A61B 5/00* (2006.01)
(Continued)

(52) U.S. Cl.
CPC ......... *A61M 25/0127* (2013.01); *A61B 5/062* (2013.01); *A61B 5/6852* (2013.01);
(Continued)

(58) Field of Classification Search
CPC .................................................. A61M 25/0127
(Continued)

(56) References Cited

U.S. PATENT DOCUMENTS 4,543,954 A * 10/1985 Cook .................. A61N 1/3655
607/21
5,644,230 A    7/1997 Pant et al.
(Continued)

FOREIGN PATENT DOCUMENTS

EP    3 139 189    *  8/2016
EP    3139189 A1    3/2017
(Continued)

OTHER PUBLICATIONS

International Search Report and Written Opinion issued in PCT/US2019/013651, dated May 2, 2019, 12 pages.

*Primary Examiner* — Stanley Tso
(74) *Attorney, Agent, or Firm* — Nelson Mullins Riley & Scarborough LLP

(57) ABSTRACT

A sensor assembly includes a multilayer circuit, a first magnetic field sensor, and a second magnetic field sensor. The multilayer circuit extends between a proximal end and a distal end along a longitudinal axis. The multilayer circuit includes a plurality of electrical pads positioned at the proximal end. The first magnetic field sensor is coupled to the multilayer circuit and has a primary sensing direction aligned with the longitudinal axis. The second magnetic field sensor is coupled to the multilayer circuit and oriented with respect to the first magnetic field sensor such that the second magnetic field sensor has a primary sensing direction aligned with an axis orthogonal to the longitudinal axis.

16 Claims, 8 Drawing Sheets

Related U.S. Application Data

(60) Provisional application No. 62/617,925, filed on Jan. 16, 2018.

(51) Int. Cl.
*A61B 5/06* (2006.01)
*A61M 25/00* (2006.01)
*G01B 7/004* (2006.01)
*H05K 1/02* (2006.01)
*H05K 1/11* (2006.01)
*H05K 1/18* (2006.01)
*H05K 3/28* (2006.01)
*H05K 3/30* (2006.01)
*H05K 7/14* (2006.01)

(52) U.S. Cl.
CPC ......... *A61M 25/0012* (2013.01); *G01B 7/004* (2013.01); *H05K 1/028* (2013.01); *H05K 1/111* (2013.01); *H05K 1/181* (2013.01); *H05K 3/284* (2013.01); *H05K 3/303* (2013.01); *H05K 7/1427* (2013.01); *A61B 5/6851* (2013.01); *A61B 5/686* (2013.01); *A61B 2562/0223* (2013.01); *A61B 2562/043* (2013.01); *A61B 2562/164* (2013.01); *A61M 2025/0166* (2013.01); *H05K 2201/056* (2013.01); *H05K 2201/10151* (2013.01)

(58) Field of Classification Search
USPC .......................................................... 604/509
See application file for complete search history.

(56) References Cited

U.S. PATENT DOCUMENTS

| | | |
|---|---|---|
| 6,169,254 B1 | 1/2001 | Pant et al. |
| 6,184,680 B1 | 2/2001 | Shinoura et al. |
| 2017/0059361 A1* | 3/2017 | Nagarkar ........... G01R 33/0017 |
| 2018/0220927 A1 | 8/2018 | Kelly et al. |
| 2018/0220928 A1 | 8/2018 | Blood et al. |
| 2019/0217059 A1 | 7/2019 | Meyer et al. |

FOREIGN PATENT DOCUMENTS

| WO | 2016/171597 A1 | 10/2016 |
|---|---|---|
| WO | WO 2016/171597 | * 10/2016 |

* cited by examiner

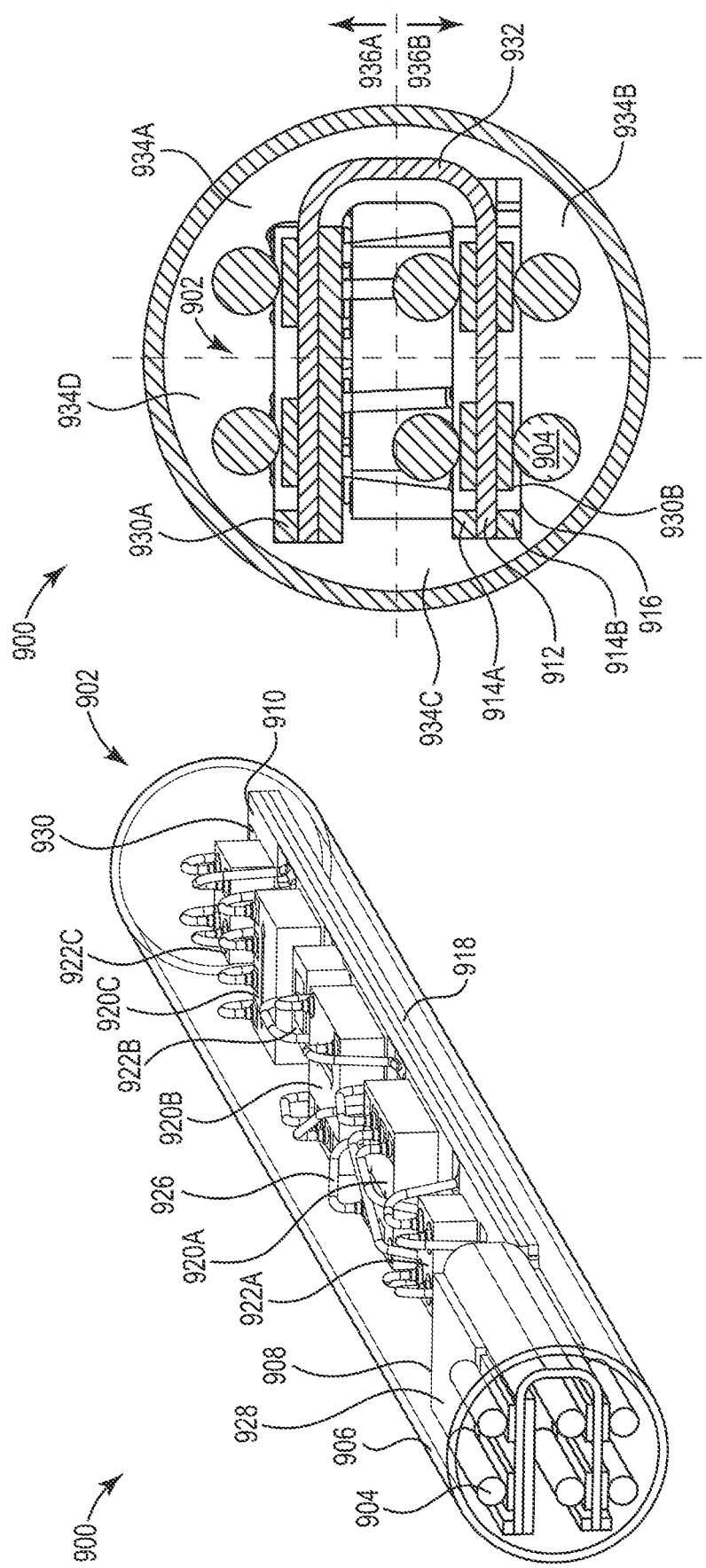

ELECTRICAL ARRANGEMENTS FOR SENSOR ASSEMBLIES IN ELECTROMAGNETIC NAVIGATION SYSTEMS

CROSS-REFERENCE TO RELATED APPLICATION

This application is a continuation application which claims priority to U.S. application Ser. No. 16/248,352, filed Jan. 15, 2019, which claims priority to Provisional Application No. 62/617,925, filed Jan. 16, 2018, which are herein incorporated by reference it its entirety.

TECHNICAL FIELD

The present disclosure relates to systems, methods, and devices for tracking items. More specifically, the disclosure relates to systems, methods, and devices for electro-magnetically tracking medical devices used in medical procedures.

BACKGROUND

A variety of systems, methods, and devices can be used to track medical devices. Tracking systems can use generated magnetic fields that are sensed by at least one tracking sensor in the tracked medical device. The generated magnetic fields provide a fixed frame of reference, and the tracking sensor senses the magnetic fields to determine the location and orientation of the sensor in relation to the fixed frame of reference.

SUMMARY

In Example 1, a sensor assembly includes a multilayer circuit, a first magnetic field sensor, and a second magnetic field sensor. The multilayer circuit extends between a proximal end and a distal end along a longitudinal axis. The multilayer circuit includes a plurality of electrical pads positioned at the proximal end. The first magnetic field sensor is coupled to the multilayer circuit and has a primary sensing direction aligned with the longitudinal axis. The second magnetic field sensor is coupled to the multilayer circuit and oriented with respect to the first magnetic field sensor such that the second magnetic field sensor has a primary sensing direction aligned with an axis orthogonal to the longitudinal axis.

In Example 2, the sensor assembly of Example 1, wherein the multilayer circuit includes a flexible substrate layer, wherein a first subset of the plurality of electrical pads is positioned on a first side of the flexible substrate layer, and wherein a second subset of the plurality of electrical pads is positioned on a second side of the flexible substrate layer opposite the first side.

In Example 3, the sensor assembly of any of Examples 1-2, wherein a proximal section of the multilayer circuit is folded such that at least one of the plurality of electrical pads is positioned on a different plane than the other plurality of electrical pads.

In Example 4, the sensor assembly of any of Examples 1-3, wherein a proximal section of the multilayer circuit is substantially c-shaped.

In Example 5, the sensor assembly of any of Examples 3-4, wherein the proximal section includes a fold portion only partially covered by a mask layer such that a portion of the flexible substrate layer is exposed.

In Example 6, the sensor assembly of any of Examples 1-5, wherein the multilayer circuit includes six to nine electrical pads at the proximal end.

In Example 7, the sensor assembly of any of Examples 1-6, further comprising a plurality of electrical leads, each electrically coupled to one of the plurality of electrical pads.

In Example 8, the sensor assembly of any of Examples 1-7, further comprising a housing surrounding the multilayer circuit, the first magnetic sensor, and the second magnetic sensor.

In Example 9, the sensor assembly of Example 8, wherein the housing includes four quadrants of substantially equal size, wherein at least one electrical lead is positioned within each of the four quadrants.

In Example 10, the sensor assembly of any of Examples 8-9, wherein the housing is cylinder, polygon, or rectangular shaped.

In Example 11, the sensor assembly of any of Examples 8-10, wherein the housing has a cross-section area of 0.096-0.79 $mm^2$.

In Example 12, the sensor assembly of any of Examples 8-11, wherein the housing comprises epoxy.

In Example 13, the sensor assembly of any of Examples 8-12, wherein the housing includes an outer shell.

In Example 14, the sensor assembly of any of Examples 1-13, wherein the first magnetic field sensor and the second magnetic field sensors include one of inductive sensing coils, magneto-resistive sensing elements, giant magneto-impedance sensing elements, and flux-gate sensing elements.

In Example 15, the sensor assembly of any of Examples 1-14, wherein the first magnetic field sensor or the second magnetic field sensor is a multi-axis sensor and includes a second primary sensing direction.

In Example 16, a system includes a sensor assembly having a multilayer circuit, a first magnetic field sensor, and a second magnetic field sensor. The multilayer circuit includes a proximal section, a distal section, and a longitudinal axis. The proximal section includes a plurality of electrical pads and is at least partially folded. The first magnetic field sensor is coupled to the multilayer circuit at the distal section and has a primary sensing direction aligned with the longitudinal axis. The second magnetic field sensor is coupled to the multilayer circuit at the distal section and oriented with respect to the first magnetic field sensor such that the second magnetic field sensor has a primary sensing direction aligned with an axis orthogonal to the longitudinal axis.

In Example 17, the system of Example 16, wherein the multilayer circuit includes a flexible substrate layer, wherein a first subset of the plurality of electrical pads is positioned on a first side of the flexible substrate layer, and wherein a second subset of the plurality of electrical pads is positioned on a second side of the flexible substrate layer opposite the first side.

In Example 18, the system of Example 16, wherein the proximal section of the multilayer circuit is substantially c-shaped.

In Example 19, the system of Example 16, wherein the proximal section of the multilayer circuit includes a flexible substrate only partially covered by a mask layer such that a portion of the flexible substrate layer is exposed.

In Example 20, the system of Example 16, wherein the multilayer circuit includes six to nine electrical pads at the proximal section.

In Example 21, the system of Example 20, further comprising a plurality of electrical leads, each electrically coupled to one of the plurality of electrical pads.

In Example 22, the system of Example 16, further comprising a housing surrounding the multilayer circuit, the first magnetic sensor, and the second magnetic sensor.

In Example 23, the system of Example 22, wherein the housing includes four quadrants of substantially equal size, wherein at least one electrical lead is positioned within each of the four quadrants.

In Example 24, the system of Example 22, wherein the housing is cylinder, polygon, or rectangular shaped.

In Example 25, the system of Example 22, wherein the housing has a cross-section area of 0.096-0.79 mm$^2$.

In Example 26, the system of Example 22, wherein the housing comprises epoxy.

In Example 27, the system of Example 22, wherein the housing comprises an outer shell and is at least partially filled with epoxy.

In Example 28, the system of Example 16, further comprising a third magnetic field sensor coupled to the multilayer circuit at the distal section and oriented with respect to the first magnetic field sensor such that the third magnetic field sensor has a primary sensing direction orthogonal to the longitudinal axis.

In Example 29, the system of Example 16, wherein the proximal section includes a first leg portion, a second leg portion, and a bend portion positioned between the first leg portion and the second leg portion.

In Example 30, the system of Example 29, wherein a first subset of the plurality of electrical pads is positioned on the first leg portion, and wherein a second subset of the plurality of electrical pads is positioned on the second leg portion.

In Example 31, the system of Example 16, wherein the first magnetic field sensor or the second magnetic field sensor is a multi-axis sensor and includes a second primary sensing direction.

In Example 32, the system of any of Examples 16-31, further comprising a medical device, wherein the sensor assembly is positioned within the medical device.

In Example 33, a method is disclosed for forming a multilayer circuit having a proximal section, a distal section, a first set of a plurality of electrical pads positioned at the proximal section, and a second set of a plurality of electrical pads positioned at the distal section. The method includes electrically coupling a plurality of magnetic field sensors to the second set of the plurality of electrical pads, electrically coupling a plurality of electrical leads each to one of the first set of the plurality of electrical pads while such electrical pads are positioned within substantially the same plane, and folding the proximal section such that the proximal section includes a bend portion having a substantially constant bending radius such that the first set of the plurality of electrical pads are no longer positioned within substantially the same plane.

In Example 34, the method of Example 33, further comprising after the folding step, positioning the multilayer circuit into a housing.

In Example 35, the method of any of Examples 33-34, further comprising after the folding step, encapsulating at least a portion of the multilayer circuit in epoxy.

In Example 36, a medical device comprising the sensor assembly of any of Examples 1-15.

In Example 37, the medical device of Example 36, wherein the medical device is a catheter.

In Example 38, the medical device of Example 37, wherein the sensor assembly is positioned within the catheter.

In Example 39, the medical device of Example 37, wherein the sensor assembly is positioned at or near a distal end of the catheter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9 shows a cross-section perspective view of a sensor assembly, in accordance with certain embodiments of the present disclosure.

FIG. 10 shows a cross-section, side view of the sensor assembly of FIG. 9.

Figure 1:
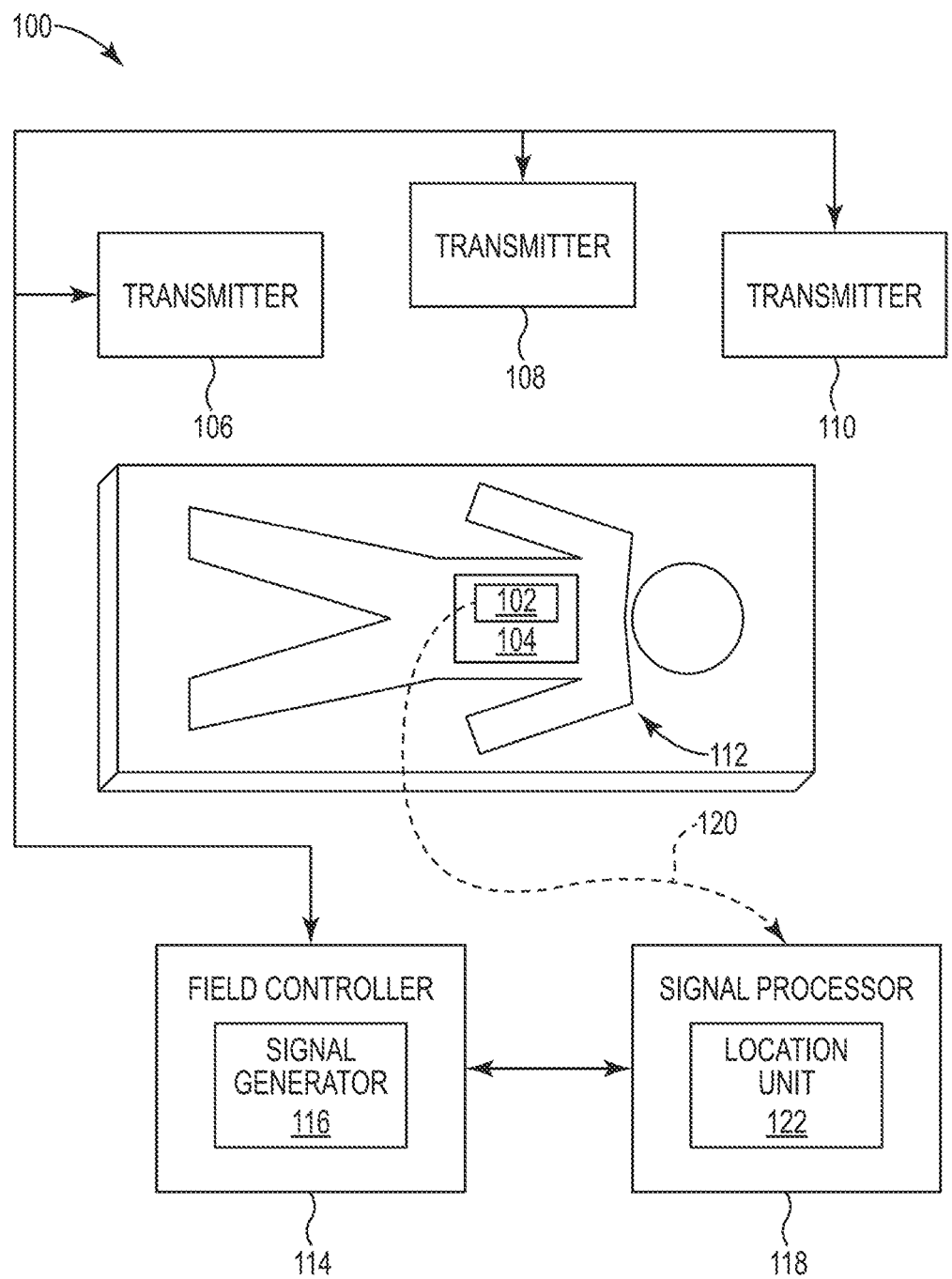
FIG. 1 shows a schematic of a tracking system, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

During medical procedures, medical devices such as probes (e.g., catheters, guidewires, scopes) are inserted into a patient. To track the location and orientation of a probe within the patient, probes can be provisioned with magnetic field sensors that detect various magnetic fields generated by transmitters near the patient.

FIG. 1 is a schematic block diagram depicting a tracking system 100 that is configured to determine location information corresponding to the medical device 104 based on information collected using a receiver (e.g., sensor) 102 associated with a medical device 104. The information collected by the receiver 102 includes a received field signal corresponding to an electromagnetic field defined by a set of electromagnetic signals transmitted by one or more magnetic field transmitter assemblies 106, 108, and 110. According to embodiments, one or more magnetic field transmitter assemblies 106, 108, and 110, are configured to transmit (e.g., radiate) electromagnetic signals, which produce a magnetic field within which a subject 112 is disposed. According to embodiments, the system 100 includes a magnetic field controller 114 configured to manage operation of the magnetic field transmitter assemblies 106, 108, and 110.

The receiver 102 (e.g., magnetic field sensor) (which may include one or more receivers/sensors) may be configured to produce an electrical response to the magnetic field(s) generated by the magnetic field transmitter assemblies 106, 108, and 110. For example, the receiver 102 may include one or more magnetic field sensors such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or flux-gate sensing elements. The receiver 102 is configured to sense the generated magnetic fields and provide tracking signals indicating the location and orientation of the receiver 102 in up to six degrees of freedom (i.e., x, y, and z measurements, and pitch, yaw, and roll angles). Generally, the number of degrees of freedom that a tracking system is able to track depends on the number of magnetic field sensors and magnetic field generators. For example, a tracking system with a single magnetic field sensor may not be capable of tracking roll angles and thus are limited to tracking in only five degrees of freedom (i.e., x, y, and z coordinates, and pitch and yaw angles). This is because a magnetic field sensed by a single magnetic field sensor does not change as the single magnetic field sensor is "rolled." The magnetic field sensors can be powered by voltages or currents to drive or excite elements of the magnetic field sensors. The magnetic field sensor elements receive the voltage or current and, in response to one or more of the generated magnetic fields, the magnetic field sensor elements generate sensing signals, which are transmitted to the magnetic field controller 114.

As shown in FIG. 1, the magnetic field controller 114 includes a signal generator 116 configured to provide driving current to each of the magnetic field transmitter assemblies 106, 108, and 110, causing each magnetic field transmitter assembly to transmit an electromagnetic signal. In certain embodiments, the signal generator 116 is configured to provide variable (e.g., sinusoidal) driving currents to the magnetic field transmitter assemblies 106, 108, and 110. The magnetic field controller 114 can be implemented using firmware, integrated circuits, and/or software modules that interact with each other or are combined together. For example, the magnetic field controller 114 may include computer-readable instructions/code for execution by a processor (see FIG. 2). Such instructions may be stored on a non-transitory computer-readable medium (see FIG. 2) and transferred to the processor for execution. In some embodiments, the magnetic field controller 114 can be implemented in one or more application-specific integrated circuits and/or other forms of circuitry suitable for controlling and processing magnetic tracking signals and information.

The sensed magnetic field signal may include multiple magnetic field signals, each of which may be processed to extract field components corresponding to one or more magnetic field transmitter assemblies. The sensed magnetic field signal is communicated to a signal processor 118, which is configured to analyze the sensed magnetic field signal to determine location information corresponding to the receiver 102 (and, thus, the medical device 104). Location information may include any type of information associated with a location and/or position of a medical device 104 such as, for example, location, relative location (e.g., location relative to another device and/or location), position, orientation, velocity, acceleration, and/or the like. As mentioned above, rotating magnetic field-based tracking can utilize phase (e.g., differences in phase) of the sensed magnetic field signal to determine location and orientation of the probe.

The tracking system 100 can also include at least one sensor that is configured and arranged to sense the magnetic fields generated by the magnetic field transmitter assemblies, 106-110. The sensor can be a magnetic sensor (e.g., dual-axis magnetic sensor, tri-axis magnetic sensor) and be positioned at a known reference point in proximity to the magnetic field transmitter assemblies, 106-110, to act as a reference sensor. For example, one or more sensors can be coupled to the subject's bed, the subject herself, an arm of an x-ray machine, or at other points a known distance from the magnetic field transmitter assemblies, 106-110. In some embodiments, the at least one sensor is mounted to one of the magnetic field transmitter assemblies, 106-110.

The medical device 104 may include, for example, a catheter (e.g., a mapping catheter, an ablation catheter, a diagnostic catheter, an introducer), an endoscopic probe or cannula, an implantable medical device (e.g., a control device, a monitoring device, a pacemaker, an implantable cardioverter defibrillator (ICD), a cardiac resynchronization therapy (CRT) device, a CRT-D), guidewire, endoscope, biopsy needle, ultrasound device, reference patch, robot and/or the like. For example, in embodiments, the medical device 104 may include a mapping catheter associated with an anatomical mapping system. The medical device 104 may include any other type of device configured to be at least temporarily disposed within a subject 112. The subject 112 may be a human, a dog, a pig, and/or any other animal having physiological parameters that can be recorded. For example, in embodiments, the subject 112 may be a human patient.

As shown in FIG. 1, the medical device 104 may be configured to be disposed within the body of a subject 112, and may be configured to be communicatively coupled to the signal processor 118 via a communication link 120 (shown in phantom). In embodiments, the communication link 120 may be, or include, a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices, and should not be understood to be limited to a direct, persistent, or otherwise limited communication channel. That is, in some embodiments, the communication link 120 may be a persistent communication link, an intermittent communication link, an ad-hoc communication link, and/or the like. The communication link 120 may refer to direct communications between the medical device 104 and the signal processor 118, and/or indirect communications that travel between the medical device 104 and the signal processor 118 via at least one other device (e.g., a repeater, router, hub, and/or the like). The communication link 120 may facilitate uni-directional and/or bi-directional communication between the medical device 104 and the signal processor 118. Data and/or control signals may be transmitted between the medical device 104 and the signal processor 118 to coordinate the functions of the medical device 104 and/or the signal processor 118.

The signal processor 118 further includes a location unit 122 configured to determine, based on the sensed field signal (e.g., the phase, amplitude, differences in phase and/or amplitude of the sensed field signal), location information corresponding to the medical device 104. The location unit 122 may be configured to determine location information according to any location-determination technique that uses magnetic navigation. According to various embodiments of the disclosed subject matter, any number of the components depicted in FIG. 1 (e.g., the field controller 114, the signal generator 116, the signal processor 118) may be implemented on one or more computing devices, either as a single unit or a combination of multiple devices. The system 100 can include a display for visualizing the position and/or orientation of the medical device 104 in the subject 112.

Figure 2:
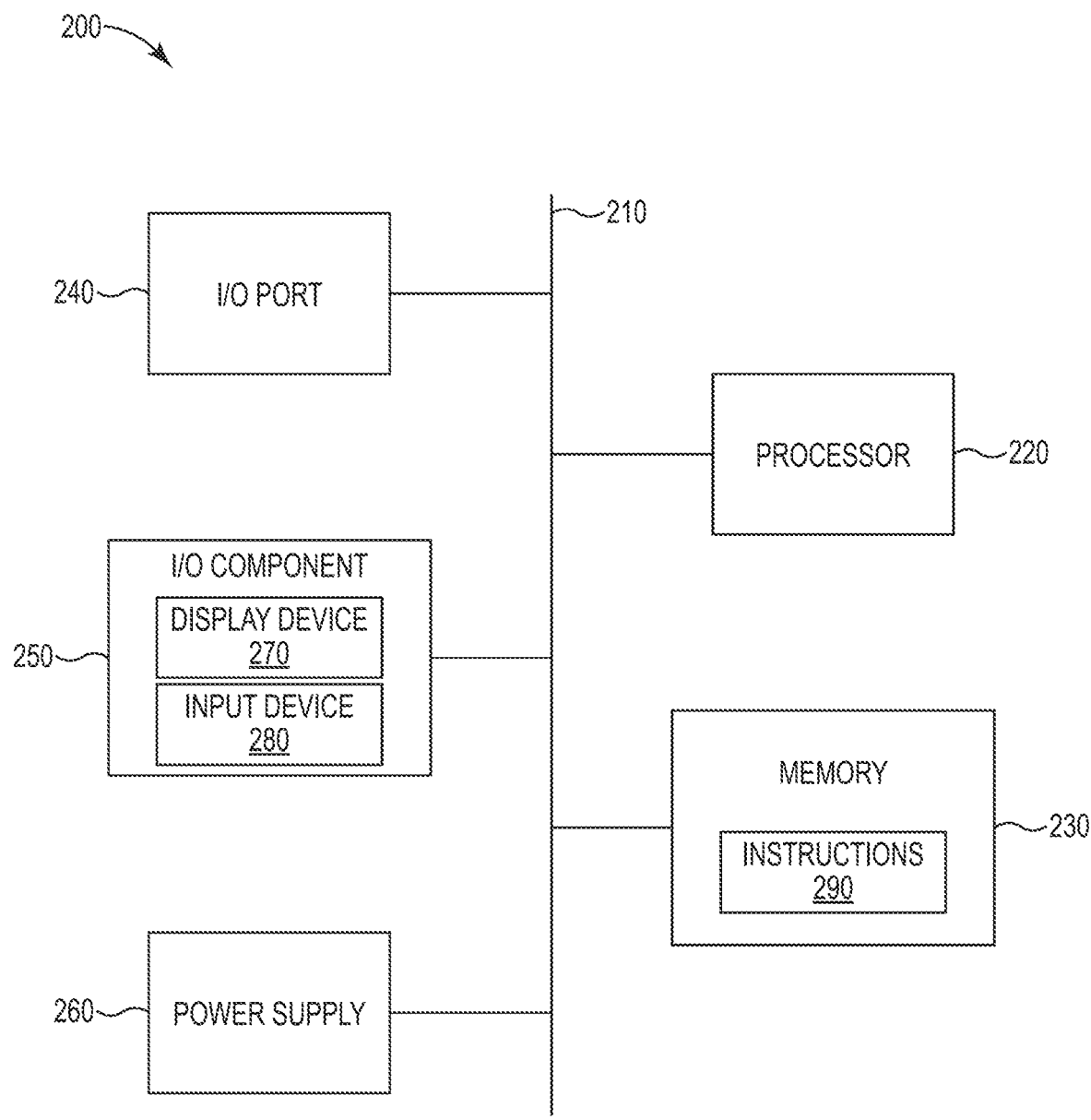
FIG. 2 shows a block representation of a computing device, in accordance with certain embodiments of the present disclosure.

FIG. 2 is a schematic block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIGS. 1 and 2, with reference to various components of the tracking system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices. As an example only, the processor 220 may include the signal processor 118, but other suitable configurations are also contemplated to suit different applications.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 290 for causing the processor 220 to implement aspects of embodiments of system components discussed herein and/or to perform aspects of embodiments of methods and procedures discussed herein.

The computer-executable instructions 290 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
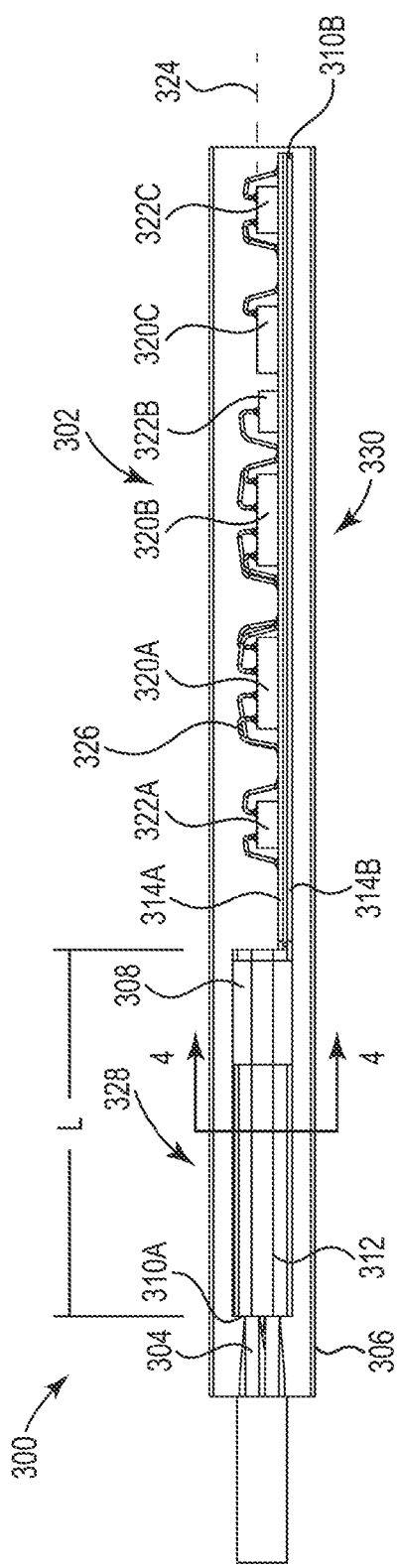
FIG. 3 shows a side view of a sensor assembly, in accordance with certain embodiments of the present disclosure.
Figure 4:
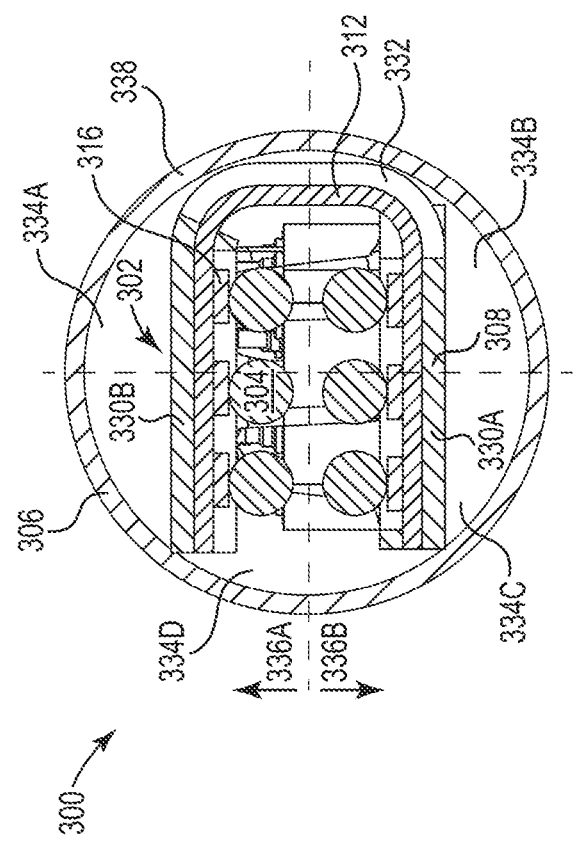
FIG. 4 shows a cross-section, side view of the sensor assembly of FIG. 3.
Figure 5:
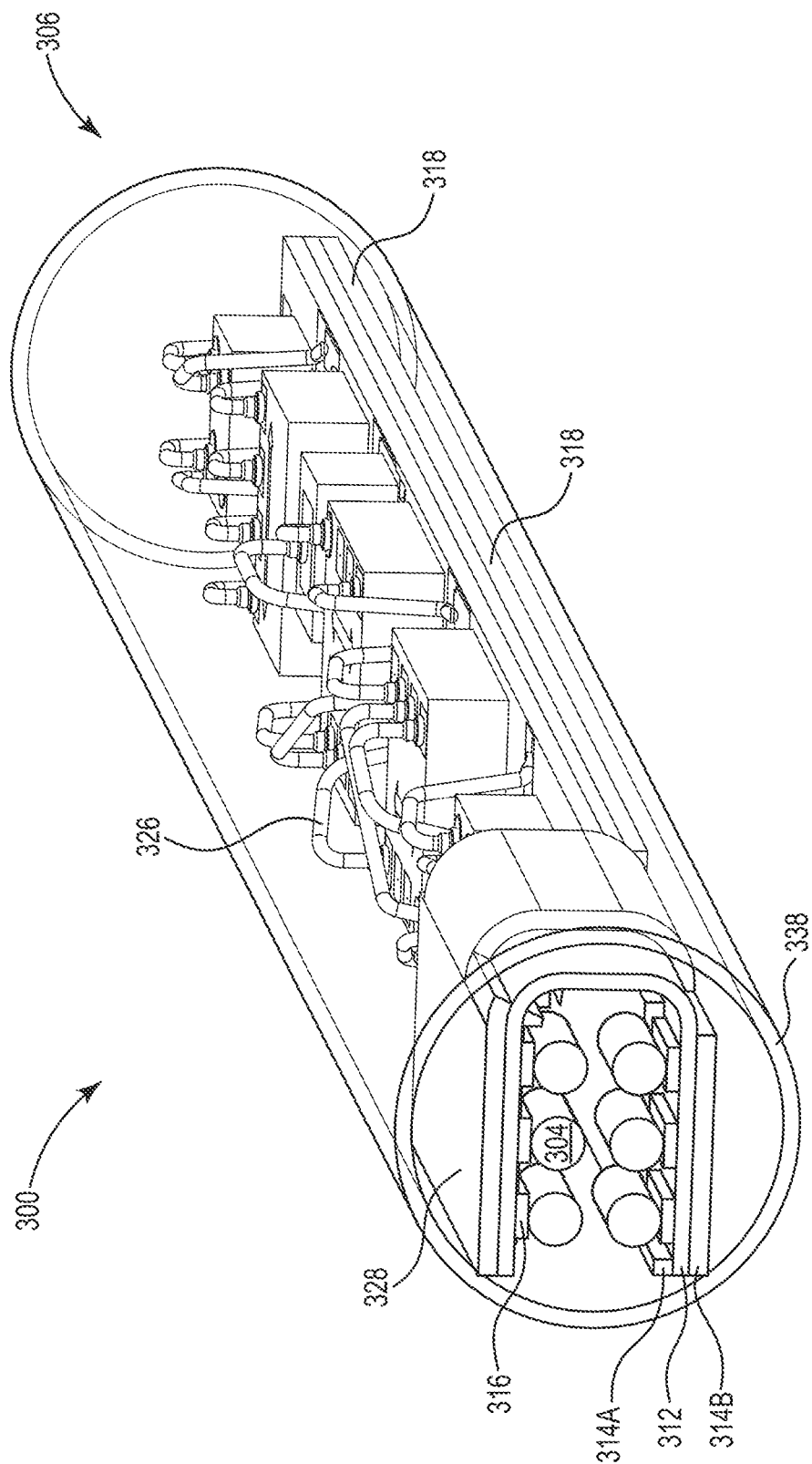
FIG. 5 shows a cross-section, perspective view of the sensor assembly of FIG. 3.
Figure 6:
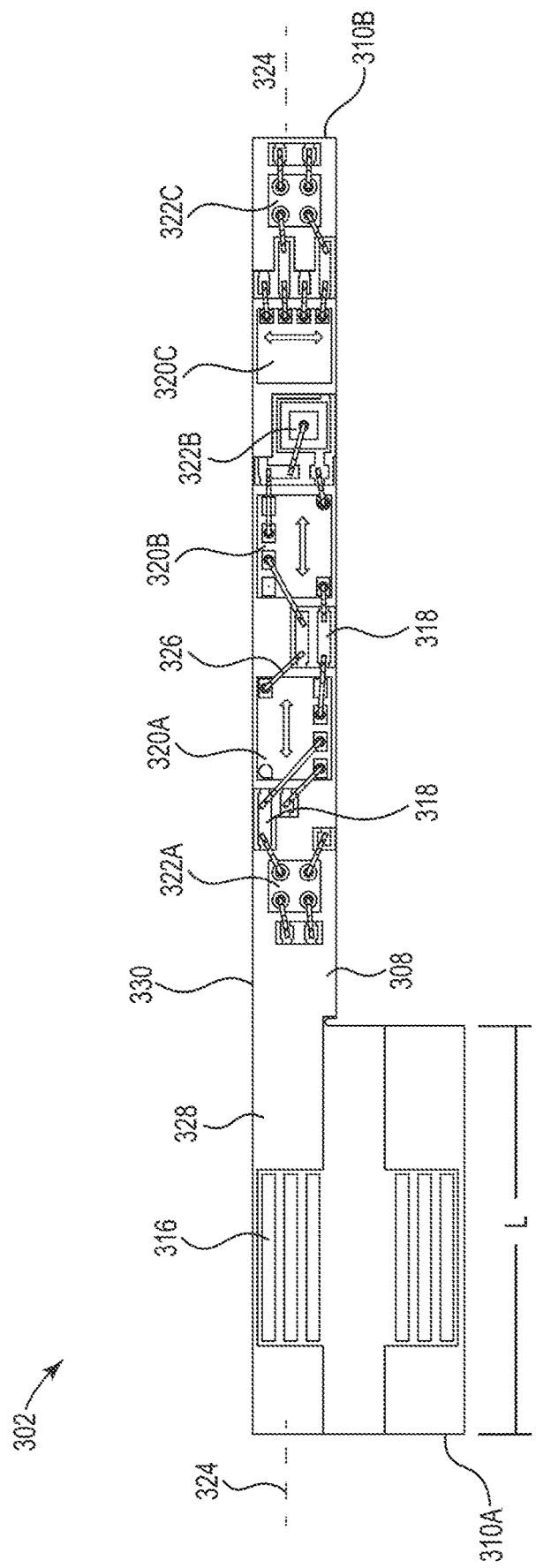
FIG. 6 shows a top view of the multilayer circuit assembly of FIG. 3.

FIGS. 3-5 show a sensor assembly 300 that can be used in a medical device (like the medical device 104 in FIG. 1). For example, the sensor assembly 300 can be positioned within the medical device (e.g., at or near a distal end of the medical device). The sensor assembly 300 includes a multilayer circuit assembly 302 electrically coupled to electrical leads 304 and positioned within a housing 306. FIG. 6 shows the multilayer circuit assembly 302 before a multilayer circuit 308 is formed into its final shape and before the multilayer circuit assembly 302 is incorporated into the sensor assembly 300.

The multilayer circuit assembly 302 includes a multilayer circuit 308 extending between a proximal end 310A and a distal end 310B. The multilayer circuit 308 comprising a flexible substrate 312 (e.g., polyimide, polyester/PET, PEEK, parylene, LCP, PEN, PEI, FEP), a first mask layer 314A, a second mask layer 314B, electrical lead pads 316 (see FIGS. 4-6), electrical mounting pads 318 (see FIGS. 5-6), and electrical traces (not shown) that electrically couple certain electrical lead pads 316 to certain electrical mounting pads 318. The first mask layer 314A and the second mask layer 314B are positioned on opposite sides of the flexible substrate 312. In certain embodiments, the multilayer circuit 308 is 5-100 microns thick.

The multilayer circuit assembly 302 further includes first, second, and third magnetic field sensors, 320A, 320B, and 320C, and first, second, and third sensor circuits 322A, 322B, and 322C (e.g., application-specific integrated circuits (ASICs), circuits with diode(s) and capacitor(s)). As shown in FIGS. 3-6, the magnetic field sensors, 320A-320C, and the sensor circuits, 322A-322C, can be implemented on separate dies and positioned next to each other. In such embodiments, the magnetic field sensors, 320A-320C, and the sensor circuits, 322A-322C, can be electrically and communicatively coupled together. In certain embodiments, respective magnetic field sensors, 320A-320C, and the sensor circuits, 322A-322C, can be implemented on the same die or substrate (e.g., a monolithic design). For example, the magnetic field sensors, 320A-320C, can be fabricated on top of respective sensor circuits, 322A-322C.

The magnetic field sensors 320A, 320B, and 320C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field transmitter assemblies, 106-110 of FIG. 1, and generate a responsive sensing signal. In addition, the multilayer circuit assembly 302 can feature other types of sensors, such as temperature sensors, ultrasound sensors, etc. Sensing signals generated by the magnetic field sensors 320A-320C can be transmitted from the sensor assembly 300 to a controller, such as the magnetic field controller 114 of FIG. 1, wirelessly or via one or more conductors.

In certain embodiments, the magnetic field sensors 320A-320C are arranged in a dual-axis, six degree-of-freedom arrangement. In such embodiments, the first magnetic field sensor 320A and the second magnetic field sensor 320B are oriented such that their primary sensing direction is aligned along a longitudinal axis 324 (e.g., X-axis) of the sensor assembly 300. The third magnetic field sensor 320C is oriented such that its primary sensing direction is aligned along an axis (e.g., Y-axis) orthogonal to the longitudinal axis 324. In certain embodiments, the magnetic field sensors 320A-320C are arranged in a tri-axis, six degree-of-freedom arrangement. In such embodiments, the magnetic field sensors' primary sensing directions are orthogonal to each other. Although the first, second, and third magnetic field sensors, 320A, 320B, and 320C, and the first, second, and third sensor circuits, 322A, 322B, and 322C are shown as being generally oriented within the same plane, the magnetic field sensors can be oriented in different planes (e.g., orthogonal planes). Although FIGS. 3-6 show the magnetic field sensors 320A-320C and the sensor circuits 322A-322C as being positioned on the same side of the multilayer circuit 308, the magnetic field sensors 320A-320C and the sensor circuits 322A-322C can be distributed between both sides of the multilayer circuit 308. Example orientations of magnetic field sensors on a sensor assembly are disclosed in U.S. Patent Application No. 62/455,339, entitled "SENSOR ASSEMBLIES FOR ELECTROMAGNETIC NAVIGATION SYSTEMS", which is herein incorporated by reference for the purposes of disclosing orientations of magnetic field sensors on a sensor assembly. In certain embodiments, the multilayer circuit assembly 302 only includes two magnetic field sensors having different primary sensing directions. In certain embodiments, one or more of the magnetic field sensors is a dual-axis or tri-axis sensor having two or three primary sensing directions, respectively. The first, second, and third magnetic field sensors, 320A-320C, are configured to generate, in response to a magnetic field, responsive sensing signals. The sensing signals are used to determine location and orientation of the sensor assembly 300.

In certain embodiments, the magnetic field sensors, 320A-320C, and/or the sensor circuits, 322A-322C, are electrically coupled to respective electrical mounting pads 318 via wire bonds 326. In some embodiments, the magnetic field sensors, 320A-320C, and/or the sensor circuits, 322A-322C, are electrically coupled to respective electrical mounting pads 318 via a flip-chip fashion, through-silicon vias, fan-out wafer-level packaging, or other form of packaging known to the art. As previously mentioned, the electrical mounting pads 318 are electrically coupled to the electrical lead pads 316 by electrical traces. Example electrical connections among magnetic field sensors, sensor circuits, electrical lead pads, and electrical mounting pads are disclosed in U.S. Patent Application No. 62/455,299, entitled "ELECTROMAGNETIC NAVIGATION SYSTEM WITH MAGNETO-RESISTIVE SENSORS AND APPLICATION-SPECIFIC INTEGRATED CIRCUITS", which is hereby incorporated by reference for the purposes of disclosing example electrical connections.

In certain embodiments, when the magnetic field sensors 320A-320C are arranged in either a dual-axis or tri-axis arrangement, the multilayer circuit 308 includes six or seven electrical lead pads 316, and the multilayer circuit assembly 302 includes six or seven electrical leads 304. In the dual-axis arrangement, the multilayer circuit assembly 302 can include six electrical lead pads 316: one ground lead pad, one bias lead pad, one positive X-axis signal lead pad, one negative X-axis signal lead pad, one positive Y-axis signal lead pad, and one negative Y-axis signal lead pad. In the tri-axis arrangement, the multilayer circuit assembly 302 can include eight or nine electrical lead pads: one ground lead pad, one bias lead pad, one positive X-axis signal lead pad, one negative X-axis signal lead pad, one positive Y-axis signal lead pad, one negative Y-axis signal lead pad, one positive Z-axis signal lead pad, one negative Z-axis signal lead pad, and a reset lead pad. In certain embodiments, the electrical leads 304 comprise a conductive material (e.g., copper), and the electrical lead pads 316 are spaced from each other at the proximal end 310A for sufficient electrical isolation. In certain embodiments, the magnetic field sensors are arranged in a single-axis, five degree-of-freedom arrangement.

FIG. 6 shows the multilayer circuit assembly 302 before a multilayer circuit 308 is formed into its final shape and before the multilayer circuit assembly 302 is incorporated into the sensor assembly 300. For each of the electrical lead pads 316 and the electrical mounting pads 318, the first mask layer 314A is removed such that the pads are exposed and accessible for electrical coupling respective electrical leads 304 and the wire bonds 326, etc.

The multilayer circuit 308 includes a proximal section 328 with the exposed electrical lead pads 316 and a distal section 330 with the exposed electrical mounting pads 318. During manufacture, the electrical leads 304 can be coupled to the electrical lead pads 316 via a plurality of approaches (e.g., reflowing solder such that the solder melts and solidifies, welding (laser and the like), tape-automated bonding, thermo-compression, ultrasonic compression, anisotropic conductive film, brazing, and the like) to mechanically and electrically couple the electrical leads 304 and the electrical lead pads 316. Providing the electrical lead pads 316 on one side of the multilayer circuit 308 makes manufacturing easier, for example, because solder can be reflowed once on only one side of the multilayer circuit 308. As noted above, the magnetic field sensors, 320A-320C, and the sensor circuits 322A-322C, can be electrically coupled to the electrical mounting pads 318 via wire bonds, flip-chips, through-silicon vias, fan-out wafer-level packaging, and the like. After the various electrical couplings are made, the proximal section 328 can be folded (e.g., rolled).

As shown in FIGS. 3-5, the proximal section 328 is folded such that the multilayer circuit 308 (and therefore the multilayer circuit assembly 302) consumes a smaller cross-section area at the proximal end 310A of the multilayer circuit assembly 302. In certain embodiments, the proximal section 328 is folded and forms a substantially c-shape. In such embodiments, the proximal section 328 has a substantially constant bending radius throughout a length of the cross-section. As shown in FIG. 4, in certain embodiments, the proximal section 328 includes a first leg portion 330A and a second leg portion 330B and a bend portion 332 extending between the first leg portion 330A and the second leg portion 330B. The electrical lead pads 316 are positioned on the first leg portion 330A and the second leg portion 330B. The bend portion 332 has a substantially constant bending radius throughout its cross-section length while the first leg portion 330A and the second leg portion 330B are substantially straight. As shown in FIG. 4, once the multilayer circuit 308 is folded, the electrical leads 304 and the electrical lead pads 316 are positioned within an inner area of the proximal section 328. In other embodiments, once the multilayer circuit 308 is folded, the electrical leads 304 and the electrical lead pads 316 can be positioned outside the inner area of the proximal section 328 closer to the housing 306.

As shown in FIGS. 3 and 6, the proximal section 328 has a length, L, extending along the longitudinal axis 324. Only a portion of the proximal section 328 is covered by the second mask layer 314B such that flexible substrate 312 is exposed. Limiting coverage of the second mask layer 314B on the proximal section 328 may provide additional flexibility for folding or rolling the proximal section 328. For example, without full coverage of the second mask layer 314B, the proximal section 328 can be folded with a small bending radius. In certain embodiments, to provide additional flexibility for folding or rolling the proximal section 328, portions of one or more of the layers of the multilayer circuit 308 has a reduced thickness.

As shown in FIG. 4, the cross-section area of the housing 306 can be separated into four quadrants 334A-334D and/or an upper half 336A and a lower half 336B, with each of the quadrants 334A-334D, and the halves 336A-336B having substantially the same respective cross-sectional area. As shown in FIG. 4, when the multilayer circuit 308 is folded, at least one of the electrical leads 304 is positioned in each of the quadrants 334A-334D and the halves 336A-336B. This approach helps fully utilize the given cross-sectional area such that a sufficient number of electrical leads 304 and electrical lead pads 316 can be used without interfering with each other and without the electrical traces within the multilayer circuit 308 interfering with each other. In certain embodiments, the housing 306 has a diameter of 0.35-1 mm (i.e., cross-section area of 0.096-0.79 $mm^2$) and a length of 3-6 mm. In certain embodiments, the housing 306 has a diameter of 0.45-0.55 mm (i.e., cross-section area of 0.16-0.24 $mm^2$) and a length of 4-5 mm. In certain embodiments, the housing 306 is square or rectangular shaped. In certain embodiments the housing 306 includes an outer shell 338 comprising a material such as polyimide, PEEK, PTFE, FEP, polyurethane, silicone, parylene, metals (e.g., stainless steel, aluminum, titanium, nickel-based alloys, cobalt-base alloys, and the like), etc., and an epoxy filler material within the outer shell 338 to maintain the position of the multilayer circuit assembly 302 in the housing 306. In certain embodiments, the entire housing 306 comprises an epoxy material.

Figures 7, 8:
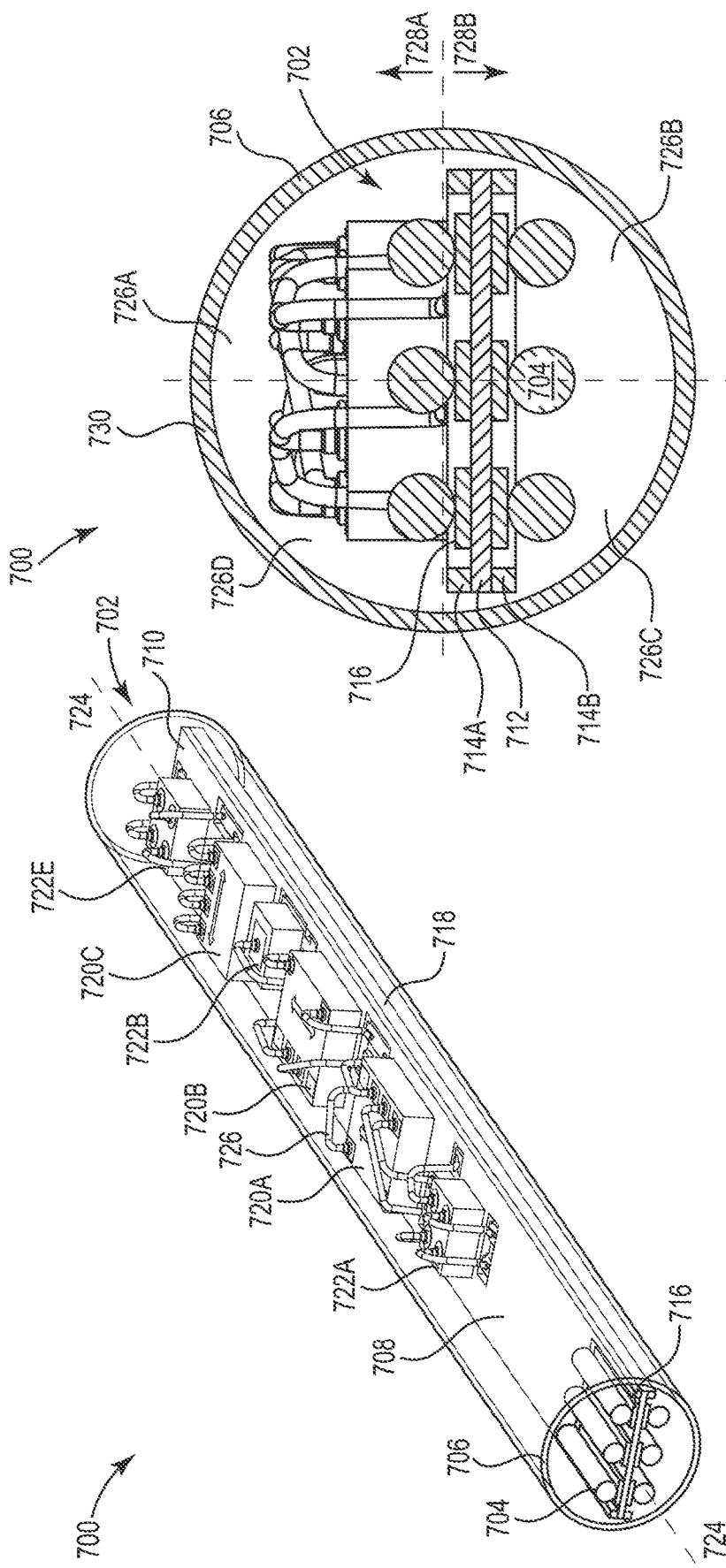
FIG. 7 shows a cross-section perspective view of a sensor assembly, in accordance with certain embodiments of the present disclosure.
FIG. 8 shows a cross-section, side view of the sensor assembly of FIG. 7.

FIGS. 7-8 show a sensor assembly 700 that can be used in a medical device (like the medical device 104 in FIG. 1). For example, the sensor assembly 300 can be positioned within the medical device (e.g., at or near a distal end of the medical device). The sensor assembly 700 includes a multilayer circuit assembly 702 electrically coupled to electrical leads 704 and positioned within a housing 706.

The multilayer circuit assembly 702 includes a multilayer circuit 708 extending between a proximal end (not shown) and a distal end 710. The multilayer circuit 708 comprising a flexible substrate 712, a first mask layer 714A, a second mask layer 714B, electrical lead pads 716, electrical mounting pads 718, and electrical traces (not shown) that electrically couple certain electrical lead pads 716 to certain electrical mounting pads 718. The first mask layer 714A and the second mask layer 714B are positioned on opposite sides of the flexible substrate 712. In certain embodiments, the multilayer circuit 708 is about 50 micrometers thick.

The multilayer circuit assembly 702 further includes first, second, and third magnetic field sensors, 720A, 720B, and 720C, and first, second, and third sensor circuits, 722A, 722B, and 722C. As shown in FIGS. 7-8, the magnetic field sensors, 720A-720C, and the sensor circuits, 722A-722C, can be implemented on separate dies and positioned next to each other. In such embodiments, the magnetic field sensors, 720A-720C, and the sensor circuits, 722A-722C, can be electrically and communicatively coupled together. In certain embodiments, respective magnetic field sensors, 720A-720C, and the sensor circuits, 722A-722C, can be implemented on the same die or substrate (e.g., a monolithic design). For example, the magnetic field sensors, 720A-720C, can be fabricated on top of respective sensor circuits, 722A-722C.

The magnetic field sensors 720A-720C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field transmitter assemblies, 106-110 of FIG. 1, and generate a responsive sensing signal. In addition, the multilayer circuit assembly 702 can feature other types of sensors, such as temperature sensors, ultrasound sensors, etc. Sensing signals generated by the magnetic field sensors 720A-720C can be transmitted from the sensor assembly 700 to a controller, such as the magnetic field controller 114 of FIG. 1, wirelessly or via one or more conductors.

In certain embodiments, the magnetic field sensors 720A-720C are arranged in a dual-axis, six degree-of-freedom arrangement. In such embodiments, the first magnetic field sensor 720A and the second magnetic field sensor 720B are oriented such that their primary sensing direction is aligned along a longitudinal axis 724 (e.g., X-axis) of the sensor assembly 700. The third magnetic field sensor 720C is oriented such that its primary sensing direction is aligned along an axis (e.g., Y-axis) orthogonal to the longitudinal axis 724. In certain embodiments, the magnetic field sensors 720A-720C are arranged in a tri-axis, six degree-of-freedom arrangement. In such embodiments, the magnetic field sensors' primary sensing directions are orthogonal to each other. Although the first, second, and third magnetic field sensors, 720A, 720B, and 720C, and the first, second, and third sensor circuits, 722A, 722B, and 722C are shown as being generally oriented within the same plane, the magnetic field sensors can be oriented in different planes (e.g., orthogonal planes). Although FIGS. 7-8 show the magnetic field sensors 720A-720C and the sensor circuits 722A-722C as being positioned on the same side of the multilayer circuit 708, the magnetic field sensors 720A-720C and the sensor circuits 722A-722C can be distributed between both sides of the multilayer circuit 708. In certain embodiments, the multilayer circuit assembly 702 only includes two magnetic field sensors having different primary sensing directions. In certain embodiments, one or more of the magnetic field sensors is a dual-axis or tri-axis sensor having two or three primary sensing directions, respectively. The first, second, and third magnetic field sensors, 720A-720C, are configured to generate, in response to a magnetic field, responsive sensing signals. The sensing signals are used to determine location and orientation of the sensor assembly 700. In certain embodiments, the magnetic field sensors are arranged in a single-axis, five degree-of-freedom arrangement.

In certain embodiments, the magnetic field sensors, 720A-720C, and/or the sensor circuits, 722A-722C, are electrically coupled to respective electrical mounting pads 718 via wire bonds 726. In some embodiments, the magnetic field sensors, 720A-720C, and/or the sensor circuits, 722A-722C, are electrically coupled to respective electrical mounting pads 718 via a flip-chip fashion, through-silicon vias, or fan-out wafer-level packaging. As previously mentioned, the electrical mounting pads 718 are electrically coupled to the electrical lead pads 716 by electrical traces.

In certain embodiments, when the magnetic field sensors 720A-720C are arranged in either a dual-axis or tri-axis arrangement, the multilayer circuit 708 includes six or seven electrical lead pads 716, and the multilayer circuit assembly 702 includes six or seven electrical leads 704. In the dual-axis arrangement, multilayer circuit assembly 702 can include six electrical lead pads 716: one ground lead pad, one bias lead pad, one positive X-axis signal lead pad, one negative X-axis signal lead pad, one positive Y-axis signal lead pad, and one negative Y-axis signal lead pad. In the tri-axis arrangement, the multilayer circuit assembly 702 can include eight or nine electrical lead pads: one ground lead pad, one bias lead pad, one positive X-axis signal lead pad, one negative X-axis signal lead pad, one positive Y-axis signal lead pad, one negative Y-axis signal lead pad, one positive Z-axis signal lead pad, one negative Z-axis signal lead pad, and a reset lead pad In certain embodiments, the electrical leads 704 comprise a conductive material (e.g., copper), and the electrical lead pads 716 are spaced from each other at the proximal end for sufficient electrical isolation.

As shown in FIGS. 7-8, the multilayer circuit 708 is not folder or rolled like the multilayer circuit 308 of FIGS. 3-6. Instead of folding or rolling, the multilayer circuit 708 is able to fit the electrical lead pads 716 into a limited cross-section area by distributing the electrical lead pads 716 between both sides of the flexible substrate 712. Further, because the multilayer circuit 708 is not folder or rolled, the multilayer circuit 708 can be rigid and utilize more rigid printed circuit boards compared to the multilayer circuit 308 of FIGS. 3-6. During manufacture, the electrical leads 704 can be coupled to the electrical lead pads 716 via a plurality of approaches (e.g., reflowing solder such that the solder melts and solidifies, welding (laser and the like), tape-automated bonding, thermo-compression, ultrasonic compression, anisotropic conductive film, brazing, and the like) to mechanically and electrically couple the electrical leads 704 and the electrical lead pads. As noted above, the magnetic field sensors, 720A-720C, and the sensor circuits 722A-722C, can be electrically coupled to the electrical mounting pads 718 via wire bonds, flip-chips, through-silicon vias, fan-out wafer-level packaging, and the like.

As shown in FIG. 8, the cross-section area of the housing 706 can be separated into four quadrants 726A-726D and/or an upper half 728A and a lower half 728B, with each of the quadrants 726A-726D, and the halves 728A-728B having substantially the same respective cross-sectional area. As shown in FIG. 8, in such a configuration, at least one of the electrical leads 704 is positioned in each of the quadrants 726A-726D and the halves 728A-728B. This approach helps fully utilize the given cross-sectional area such that a sufficient number of electrical leads 704 and electrical lead pads 716 can be used without interfering with each other and without the electrical traces within the multilayer circuit 708 from interfering with each other. In certain embodiments, the housing 706 has a diameter of 0.35-1 mm (i.e., cross-section area of 0.096-0.79 mm$^2$) and a length of 3-6 mm. In certain embodiments, the housing 706 has a diameter of 0.45-0.55 mm (i.e., cross-section area of 0.16-0.24 mm$^2$) and a length of 4-5 mm. In certain embodiments, the housing 706 is square or rectangular shaped. In certain embodiments the housing 706 includes an outer shell 730 comprising a material such as polyimide, PEEK, PTFE, FEP, polyurethane, silicone, parylene, metals (e.g., stainless steel, aluminum, titanium, nickel-based alloys, cobalt-base alloys, and the like), etc., and an epoxy filler material to maintain the position of the multilayer circuit assembly 702 in the housing 706. In certain embodiments, the entire housing 706 comprises an epoxy material.

FIGS. 9-10 show a sensor assembly 900 that can be used in a medical device (like the medical device 104 in FIG. 1). For example, the sensor assembly 300 can be positioned within the medical device (e.g., at or near a distal end of the medical device). The sensor assembly 900 includes a multilayer circuit assembly 902 electrically coupled to electrical leads 904 and positioned within a housing 906.

The multilayer circuit assembly 902 includes a multilayer circuit 908 extending between a proximal end (not shown) and a distal end 910. The multilayer circuit 908 comprising a flexible substrate 912, a first mask layer 914A, a second mask layer 914B, electrical lead pads 916, electrical mounting pads 918, and electrical traces (not shown) that electrically couple certain electrical lead pads 916 to certain electrical mounting pads 918. The first mask layer 914A and the second mask layer 914B are positioned on opposite sides of the flexible substrate 912. In certain embodiments, the multilayer circuit 908 is about 50 micrometers thick.

The multilayer circuit assembly 902 further includes first, second, and third magnetic field sensors, 920A, 920B, and 920C, and first, second, and third sensor circuits, 922A, 922B, and 922C. As shown in FIGS. 3-6, the magnetic field sensors, 920A-920C, and the sensor circuits, 922A-922C, can be implemented on separate dies and positioned next to each other. In such embodiments, the magnetic field sensors, 920A-920C, and the sensor circuits, 922A-922C, can be electrically and communicatively coupled together. In certain embodiments, respective magnetic field sensors, 920A-920C, and the sensor circuits, 922A-922C, can be implemented on the same die or substrate (e.g., a monolithic design). For example, the magnetic field sensors, 920A-920C, can be fabricated on top of respective sensor circuits, 922A-922C.

The magnetic field sensors 920A, 920B, and 920C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field transmitter assemblies, 106-110 of FIG. 1, and generate a responsive sensing signal. In addition, the multilayer circuit assembly 902 can feature other types of sensors, such as temperature sensors, ultrasound sensors, etc. Sensing signals generated by the magnetic field sensors 920A-920C can be transmitted from the sensor assembly 900 to a controller, such as the magnetic field controller 114 of FIG. 1, wirelessly or via one or more conductors.

In certain embodiments, the magnetic field sensors 920A-920C are arranged in a dual-axis, six degree-of-freedom arrangement. In such embodiments, the first magnetic field sensor 920A and the second magnetic field sensor 920B are oriented such that their primary sensing direction is aligned along a longitudinal axis 924 (e.g., X-axis) of the sensor assembly 900. The third magnetic field sensor 920C is oriented such that its primary sensing direction is aligned along an axis (e.g., Y-axis) orthogonal to the longitudinal axis 924. In certain embodiments, the magnetic field sensors 920A-920C are arranged in a tri-axis, six degree-of-freedom arrangement. In such embodiments, the magnetic field sensors' primary sensing directions are orthogonal to each other. Although the first, second, and third magnetic field sensors, 920A, 920B, and 920C, and the first, second, and third sensor circuits, 922A, 922B, and 922C are shown as being generally oriented within the same plane, the magnetic field sensors can be oriented in different planes (e.g., orthogonal planes). Although FIGS. 9-10 show the magnetic field sensors 920A-920C and the sensor circuits 922A-922C as being positioned on the same side of the multilayer circuit 908, the magnetic field sensors 920A-920C and the sensor circuits 922A-922C can be distributed between both sides of the multilayer circuit 908. In certain embodiments, the multilayer circuit assembly 902 only includes two magnetic field sensors having different primary sensing directions. In certain embodiments, one or more of the magnetic field sensors is a dual-axis or tri-axis sensor having two or three primary sensing directions, respectively. The first, second, and third magnetic field sensors, 920A-920C, are configured to generate, in response to a magnetic field, responsive sensing signals. The sensing signals are used to determine location and orientation of the sensor assembly 900.

In certain embodiments, the magnetic field sensors, 920A-920C, and/or the sensor circuits, 922A-922C, are electrically coupled to respective electrical mounting pads 918 via wire bonds 926. In some embodiments, the magnetic field sensors, 920A-920C, and/or the sensor circuits, 922A-922C, are electrically coupled to respective electrical mounting pads 918 via a flip-chip fashion, through-silicon vias, or fan-out wafer-level packaging. As previously mentioned, the electrical mounting pads 918 are electrically coupled to the electrical lead pads 916 by electrical traces.

In certain embodiments, when the magnetic field sensors 920A-920C are arranged in either a dual-axis or tri-axis arrangement, the multilayer circuit 908 includes six or seven electrical lead pads 916, and the multilayer circuit assembly 902 includes six or seven electrical leads 904. In the dual-axis arrangement, multilayer circuit assembly 902 can include six electrical lead pads 916: one ground lead pad, one bias lead pad, one positive X-axis signal lead pad, one negative X-axis signal lead pad, one positive Y-axis signal lead pad, and one negative Y-axis signal lead pad. In the tri-axis arrangement, the multilayer circuit assembly 902 can include eight or nine electrical lead pads: one ground lead pad, one bias lead pad, one positive X-axis signal lead pad, one negative X-axis signal lead pad, one positive Y-axis signal lead pad, one negative Y-axis signal lead pad, one positive Z-axis signal lead pad, one negative Z-axis signal lead pad, and a reset lead pad. In certain embodiments, the electrical leads 904 comprise a conductive material (e.g., copper), and the electrical lead pads 916 are spaced from each other at the proximal end for sufficient electrical isolation.

The multilayer circuit 908 includes a proximal section 928 with the exposed electrical lead pads 916 and a distal section 930 with the exposed electrical mounting pads 918. During manufacture, the electrical leads 904 can be coupled to the electrical lead pads 916 via a plurality of approaches (e.g., reflowing solder such that the solder melts and solidifies, welding (laser and the like), tape-automated bonding, thermo-compression, ultrasonic compression, anisotropic conductive film, brazing, and the like) to mechanically and electrically couple the electrical leads 904 and the electrical lead pads 916. As noted above, the magnetic field sensors, 920A-920C, and the sensor circuits 922A-922C, can be electrically coupled to the electrical mounting pads 918 via wire bonds, flip-chips, through-silicon vias, fan-out wafer-level packaging, and the like. After the various electrical couplings are made, the proximal section 928 can be folded (e.g., rolled).

As shown in FIGS. 9-10, the proximal section 928 is folded such that the multilayer circuit 908 (and therefore the multilayer circuit assembly 902) consumes a smaller cross-section area at the proximal end of the multilayer circuit assembly 902. In certain embodiments, the proximal section 928 is folded and forms a substantially c-shape. In such embodiments, the proximal section 928 has a substantially constant bending radius throughout a length of the cross-section. As shown in FIG. 10, in certain embodiments, the proximal section 928 includes a first leg portion 930A and a second leg portion 930B and a bend portion 932 extending between the first leg portion 930A and the second leg portion 930B. The electrical lead pads 916 are positioned on the first leg portion 930A and the second leg portion 930B. The bend portion 932 has a substantially constant bending radius throughout its cross-section length while the first leg portion 930A and the second leg portion 930B are substantially straight. In addition to folding the proximal section 928, the multilayer circuit 908 distributes the electrical lead pads 916 between both sides of the flexible substrate 912. For example, the multilayer circuit 908 includes four electrical lead pads 916 on a first side of the flexible substrate 912 and two electrical lead pads on an opposite side of the flexible substrate 912. As shown in FIG. 10, once the multilayer circuit 908 is folded, the electrical leads 904 and the electrical lead pads 916 are positioned within an inner area and an outer area of the proximal section 928. In particular, two of the electrical lead pads 916 are positioned within the inner area of the folded proximal section 928 and four of the electrical lead pads 916 are positioned outside the inner area.

As shown in FIG. 10, only a portion of the proximal section 928 is covered by the second mask layer 914B such that the flexible substrate 912 is exposed. Limiting coverage of the second mask layer 914B on the proximal section 928 may provide additional flexibility for folding or rolling the proximal section 928. For example, without full coverage of the second mask layer 914B (or first mask layer 914A), the proximal section 928 can be folded with a small bending radius. In certain embodiments, to provide additional flexibility for folding or rolling the proximal section 928, portions of one or more of the layers of the multilayer circuit 908 has a reduced thickness.

As shown in FIG. 10, the cross-section area of the housing 906 can be separated into four quadrants 934A-934D and/or an upper half 936A and a lower half 936B, with each of the quadrants 934A-934D, and the halves 936A-936B having substantially the same respective cross-sectional area. As shown in FIG. 10, when the multilayer circuit 908 is folded, at least one of the electrical leads 904 is positioned in each of the quadrants 934A-934D and the halves 936A-936B. This approach helps fully utilize the given cross-sectional area such that a sufficient number of electrical leads 904 and electrical lead pads 916 can be used without interfering with each other and without the electrical traces within the multilayer circuit 908 from interfering with each other. In certain embodiments, the housing 906 has a diameter of 0.35-1 mm (i.e., cross-section area of 0.096-0.79 $mm^2$) and a length of 3-6 mm. In certain embodiments, the housing 906 has a diameter of 0.45-0.55 mm (i.e., cross-section area of 0.16-0.24 $mm^2$) and a length of 4-5 mm. In certain embodiments, the housing 906 is square or rectangular shaped. In certain embodiments the housing 906 includes an outer shell 938 comprising a material such as polyimide, PEEK, PTFE, FEP, polyurethane, silicone, parylene, metals (e.g., stainless steel, aluminum, titanium, nickel-based alloys, cobalt-base alloys, and the like), etc., and an epoxy filler material to maintain the position of the multilayer circuit assembly 902 in the housing 906. In certain embodiments, the entire housing 906 comprises an epoxy material.

Figure 11:
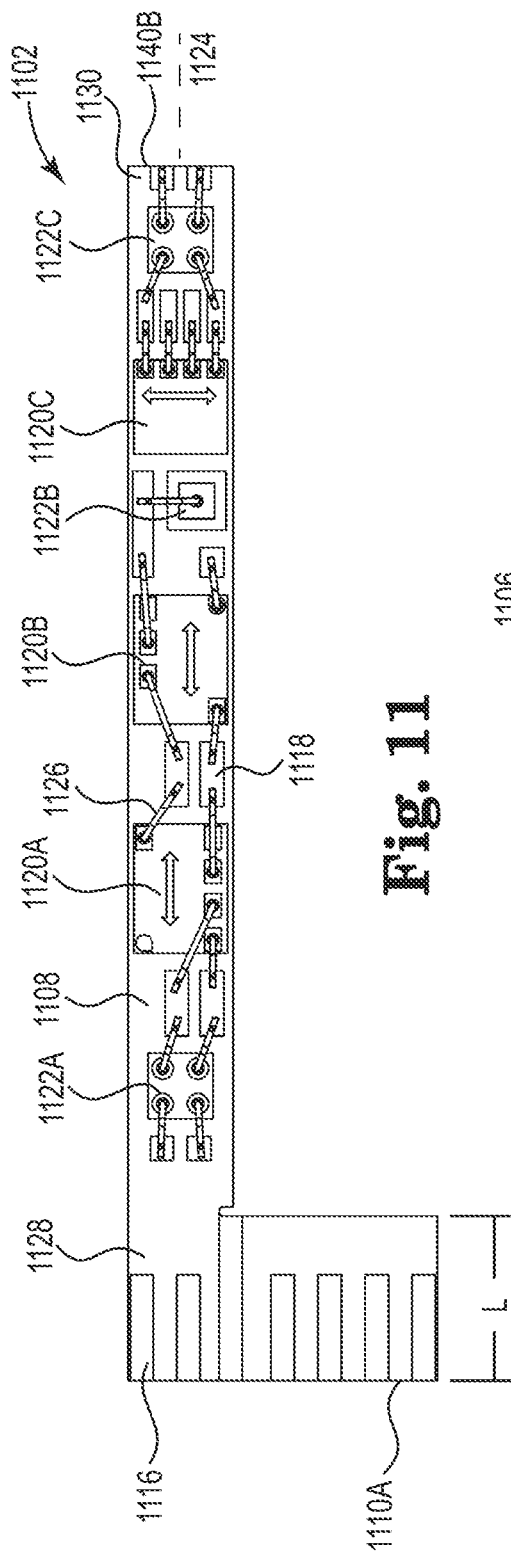
FIG. 11 shows a top view of a multilayer circuit assembly, in accordance with certain embodiments of the present disclosure.
Figure 12:
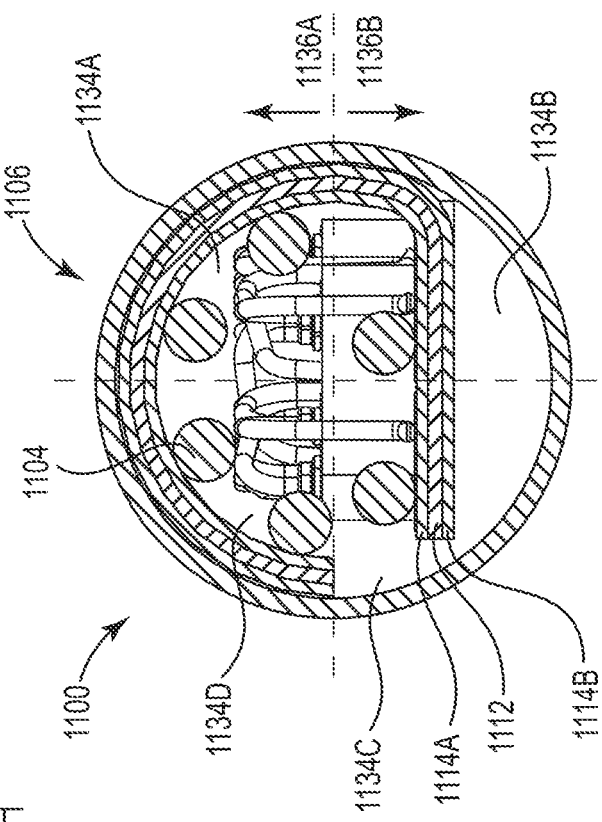
FIG. 12 shows a cross-section, side view of a sensor assembly including the multiplayer sensor assembly of FIG. 11, in accordance with certain embodiments of the present disclosure.

FIGS. 11-12 show a sensor assembly 1100 or portions thereof that can be used in a medical device (like the medical device 104 in FIG. 1). For example, the sensor assembly 300 can be positioned within the medical device (e.g., at or near a distal end of the medical device). The sensor assembly 1100 includes a multilayer circuit assembly 1102 electrically coupled to electrical leads 1104 (see FIG. 12) and positioned within a housing 1106 (see FIG. 12). FIG. 11 shows the multilayer circuit assembly 1102 before a multilayer circuit 1108 is formed into its final shape and before the multilayer circuit assembly 1102 is incorporated into the sensor assembly 1100.

The multilayer circuit assembly 1102 includes a multilayer circuit 1108 extending between a proximal end 1110A and a distal end 1110B. The multilayer circuit 1108 comprising a flexible substrate 1112, a first mask layer 1114A, a second mask layer 1114B, electrical lead pads 1116, electrical mounting pads 1118, and electrical traces (not shown) that electrically couple certain electrical lead pads 1116 to certain electrical mounting pads 1118. The first mask layer 1114A and the second mask layer 1114B are positioned on opposite sides of the flexible substrate 1112. In certain embodiments, the multilayer circuit 1108 is about 50 micrometers thick.

The multilayer circuit assembly 1102 further includes first, second, and third magnetic field sensors, 1120A, 1120B, and 1120C, and first, second, and third sensor circuits, 1122A, 1122B, and 1122C. As shown in FIGS. 11-12, the magnetic field sensors, 1120A-1120C, and the sensor circuits, 1122A-1122C, can be implemented on separate dies and positioned next to each other. In such embodiments, the magnetic field sensors, 1120A-1120C, and the sensor circuits, 1122A-1122C, can be electrically and communicatively coupled together. In certain embodiments, respective magnetic field sensors, 1120A-1120C, and the sensor circuits, 1122A-1122C, can be implemented on the same die or substrate (e.g., a monolithic design). For example, the magnetic field sensors, 1120A-1120C, can be fabricated on top of respective sensor circuits, 1122A-1122C.

The magnetic field sensors 1120A, 1120B, and 1120C can include sensors such as inductive sensing coils and/or various sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. The MR sensing elements are configured to sense magnetic fields, like those generated by the magnetic field transmitter assemblies, 106-110 of FIG. 1, and generate a responsive sensing signal. In addition, the multilayer circuit assembly 1102 can feature other types of sensors, such as temperature sensors, ultrasound sensors, etc. Sensing signals generated by the magnetic field sensors 1120A-1120C can be transmitted from the sensor assembly 1100 to a controller, such as the magnetic field controller 114 of FIG. 1, wirelessly or via one or more conductors.

In certain embodiments, the magnetic field sensors 1120A-1120C are arranged in a dual-axis, six degree-of-freedom arrangement. In such embodiments, the first magnetic field sensor 1120A and the second magnetic field sensor 1120B are oriented such that their primary sensing direction is aligned along a longitudinal axis 1124 (e.g., X-axis) of the sensor assembly 1100. The third magnetic field sensor 1120C is oriented such that its primary sensing direction is aligned along an axis (e.g., Y-axis) orthogonal to the longitudinal axis 1124. In certain embodiments, the magnetic field sensors 1120A-1120C are arranged in a tri-axis, six degree-of-freedom arrangement. In such embodiments, the magnetic field sensors' primary sensing directions are orthogonal to each other. Although the first, second, and third magnetic field sensors, 1120A, 1120B, and 1120C, and the first, second, and third sensor circuits, 1122A, 1122B, and 1122C are shown as being generally oriented within the same plane, the magnetic field sensors can be oriented in different planes (e.g., orthogonal planes). Although FIGS. 11-12 show the magnetic field sensors 1120A-1120C and the sensor circuits 1122A-1122C as being positioned on the same side of the multilayer circuit 1108, the magnetic field sensors 1120A-1120C and the sensor circuits 1122A-1122C can be distributed between both sides of the multilayer circuit 1108. In certain embodiments, the multilayer circuit assembly 1102 only includes two magnetic field sensors having different primary sensing directions. In certain embodiments, one or more of the magnetic field sensors is a dual-axis or tri-axis sensor having two or three primary sensing directions, respectively. The first, second, and third magnetic field sensors, 1120A-1120C, are configured to generate, in response to a magnetic field, responsive sensing signals. The sensing signals are used to determine location and orientation of the sensor assembly 1100.

In certain embodiments, the magnetic field sensors, 1120A-1120C, and/or the sensor circuits, 1122A-1122C, are electrically coupled to respective electrical mounting pads 1118 via wire bonds 1126. In some embodiments, the magnetic field sensors, 1120A-1120C, and/or the sensor circuits, 1122A-1122C, are electrically coupled to respective electrical mounting pads 1118 via a flip-chip fashion, through-silicon vias, or fan-out wafer-level packaging. As previously mentioned, the electrical mounting pads 1118 are electrically coupled to the electrical lead pads 1116 by electrical traces.

In certain embodiments, when the magnetic field sensors 1120A-1120C are arranged in either a dual-axis or tri-axis arrangement, the multilayer circuit 1108 includes six or seven electrical lead pads 1116, and the multilayer circuit assembly 1102 includes six or seven electrical leads 1104. In the dual-axis arrangement, multilayer circuit assembly 1102 can include six electrical lead pads 1116: one ground lead pad, one bias lead pad, one positive X-axis signal lead pad, one negative X-axis signal lead pad, one positive Y-axis signal lead pad, and one negative Y-axis signal lead pad. In the tri-axis arrangement, the multilayer circuit assembly 1102 can include eight or nine electrical lead pads: one ground lead pad, one bias lead pad, one positive X-axis signal lead pad, one negative X-axis signal lead pad, one positive Y-axis signal lead pad, one negative Y-axis signal lead pad, one positive Z-axis signal lead pad, one negative Z-axis signal lead pad, and a reset lead pad. In certain embodiments, the electrical leads 1104 comprise a conductive material (e.g., copper), and the electrical lead pads 1116 are spaced from each other at the proximal end for sufficient electrical isolation.

FIG. 11 shows the multilayer circuit assembly 1102 before a multilayer circuit 1108 is formed into its final shape and before the multilayer circuit assembly 1102 is incorporated into the sensor assembly 1100. For each of the electrical lead pads 1116 and the electrical mounting pads 1118, the first mask layer 1114A is removed such that the pads are exposed and accessible for electrical coupling respective electrical leads 1104 and the wire bonds 1126, etc.

The multilayer circuit 1108 includes a proximal section 1128 with the exposed electrical lead pads 1116 and a distal section 1130 with the exposed electrical mounting pads 1118. During manufacture, the electrical leads 1104 can be coupled to the electrical lead pads 1116 via a plurality of approaches (e.g., reflowing solder such that the solder melts and solidifies, welding (laser and the like), tape-automated bonding, thermo-compression, ultrasonic compression, anisotropic conductive film, brazing, and the like) to mechanically and electrically couple the electrical leads 1104 and the electrical lead pads 1116. As noted above, the magnetic field sensors, 1120A-1120C, and the sensor circuits 1122A-1122C, can be electrically coupled to the electrical mounting pads 1118 via wire bonds, flip-chips, through-silicon vias, fan-out wafer-level packaging, and the like. After the various electrical couplings are made, the proximal section 1128 can be folded (e.g., rolled).

As shown in FIG. 12, the proximal section 1128 is folded such that the multilayer circuit 1108 (and therefore the multilayer circuit assembly 1102) consumes a smaller cross-section area at the proximal end 1110A of the multilayer circuit assembly 1102. In certain embodiments, the proximal section 1128 is folded and forms shape that at least partially mimics a shape of the housing 1106. In such embodiments, a portion of the proximal section 1128 has a substantially constant bending radius throughout a length of the cross-section. As shown in FIG. 11, in certain embodiments, the proximal section 1128 includes a leg portion and a bend portion. The electrical lead pads 1116 are positioned on both the leg portion and the bend portion. In particular, four of the electrical lead pads 1116 are positioned on the bend portion and two of the electrical lead pads 1116 are positioned on the leg portion. The bend portion has a substantially constant bending radius throughout its cross-section length while the leg portion is substantially straight. As shown in FIG. 12, once the multilayer circuit 1108 is folded, the electrical leads 1104 and the electrical lead pads 1116 are positioned within an inner area of the proximal section 1128.

As shown in FIG. 11, the proximal section 1128 has a length, L, extending along the longitudinal axis 1124. In certain embodiments, to provide additional flexibility for folding or rolling the proximal section 1128, portions of one or more of the layers of the multilayer circuit 1108 has a reduced thickness or can be removed.

As shown in FIG. 11, the cross-section area of the housing 1106 can be separated into four quadrants 1134A-1134D and/or an upper half 1136A and a lower half 1136B, with each of the quadrants 1134A-1134D, and the halves 1136A-1136B having substantially the same respective cross-sectional area. As shown in FIG. 11, when the multilayer circuit 1108 is folded, at least one of the electrical leads 1104 is positioned in each of the quadrants 1134A-1134D and the halves 1136A-1136B. This approach helps fully utilize the given cross-sectional area such that a sufficient number of electrical leads 1104 and electrical lead pads 1116 can be used without interfering with each other and without the electrical traces within the multilayer circuit 1108 from interfering with each other. In certain embodiments, the housing 1106 has a diameter of 0.35-1 mm (i.e., cross-section area of 0.096-0.79 mm$^2$) and a length of 3-6 mm. In certain embodiments, the housing 1106 has a diameter of 0.45-0.55 mm (i.e., cross-section area of 0.16-0.24 mm$^2$) and a length of 4-5 mm. In certain embodiments, the housing 1106 is square or rectangular shaped. In certain embodiments the housing 1106 includes an outer shell 1138 comprising a material such as polyimide, PEEK, PTFE, FEP, polyurethane, silicone, parylene, metals (e.g., stainless steel, aluminum, titanium, nickel-based alloys, cobalt-base alloys, and the like), etc., and an epoxy filler material to maintain the position of the multilayer circuit assembly 1102 in the housing 1106. In certain embodiments, the entire housing 1106 comprises an epoxy material.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system comprising:
   a sensor assembly including:
   a multilayer circuit including a proximal section, a distal section, and a longitudinal axis, the proximal section including a plurality of electrical pads,
   a first magnetic field sensor coupled to the multilayer circuit at the distal section and having a primary sensing direction aligned with the longitudinal axis,
   a second magnetic field sensor coupled to the multilayer circuit at the distal section and oriented with respect to the first magnetic field sensor such that the second magnetic field sensor has a primary sensing direction aligned with an axis orthogonal to the longitudinal axis,
   a housing surrounding the multilayer circuit, the first magnetic sensor, and the second magnetic sensor, the housing having a diameter of between 0.45 mm and 0.55 mm and a length of between 4 mm and 5 mm; and wherein the multilayer circuit includes a flexible substrate layer, wherein a first subset of the plurality of electrical pads is positioned on a first major surface of the flexible substrate layer, and wherein a second subset of the plurality of electrical pads is positioned on a second major surface of the flexible substrate layer opposite the first major surface, wherein the flexible substrate layer is disposed between the first subset of the plurality of electrical pads on the first major surface and the second subset of the plurality of electrical pads on the second major surface on an axis perpendicular to the flexible substrate.

2. The system of claim 1, wherein the proximal section of the multilayer circuit is c-shaped.

3. The system of claim 1, wherein the flexible substrate layer is only partially covered by a mask layer such that a portion of the flexible substrate layer is exposed.

4. The system of claim 1, wherein the multilayer circuit includes six to nine electrical pads at the proximal section.

5. The system of claim 4, further comprising:
a plurality of electrical leads, each electrically coupled to one of the plurality of electrical pads.

6. The system of claim 1, further comprising:
a housing surrounding the multilayer circuit, the first magnetic sensor, and the second magnetic sensor.

7. The system of claim 6, wherein the housing includes four quadrants of equal size, wherein at least one electrical lead is positioned within each of the four quadrants.

8. The system of claim 6, wherein the housing is cylinder, polygon, or rectangular shaped.

9. The system of claim 6, wherein the housing has a cross-section area of 0.096-0.79 mm$^2$.

10. The system of claim 6, wherein the housing comprises epoxy.

11. The system of claim 6, wherein the housing comprises an outer shell and is at least partially filled with epoxy.

12. The system of claim 1, further comprising:
a third magnetic field sensor coupled to the multilayer circuit at the distal section and oriented with respect to the first magnetic field sensor such that the third magnetic field sensor has a primary sensing direction orthogonal to the longitudinal axis.

13. The system of claim 1, wherein the proximal section includes a first leg portion, a second leg portion, and a bend portion positioned between the first leg portion and the second leg portion.

14. The system of claim 13, wherein a first subset of the plurality of electrical pads is positioned on the first leg portion, and wherein a second subset of the plurality of electrical pads is positioned on the second leg portion.

15. The system of claim 1, wherein the first magnetic field sensor or the second magnetic field sensor is a multi-axis sensor and includes a second primary sensing direction.

16. The system of claim 1, further comprising:
a medical device, wherein the sensor assembly is positioned within the medical device.

* * * * *